(12) United States Patent
Shimizu

(10) Patent No.: US 7,575,718 B2
(45) Date of Patent: Aug. 18, 2009

(54) FLUID FEEDING SYSTEM, FLUID FEEDING METHOD AND FLOW CHANNEL UNIT

(75) Inventor: Hitoshi Shimizu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 658 days.

(21) Appl. No.: 11/436,670

(22) Filed: May 19, 2006

(65) Prior Publication Data
US 2006/0263263 A1 Nov. 23, 2006

(30) Foreign Application Priority Data
May 19, 2005 (JP) ............................. 2005-147152

(51) Int. Cl.
*G01N 33/00* (2006.01)
(52) U.S. Cl. ..................................... 422/68.1
(58) Field of Classification Search ................ 422/68.1
See application file for complete search history.

(56) References Cited
FOREIGN PATENT DOCUMENTS
JP 3294605 B2 4/2002

*Primary Examiner*—Walter D Griffin
*Assistant Examiner*—Bobby Ramdhanie
(74) *Attorney, Agent, or Firm*—Sughrue Mion, PLLC

(57) ABSTRACT

A fluid feeding system consists of a flow channel member and a fluid feeding apparatus. The flow channel member has at least a flow channel for feeding a fluid to a sensor surface. Pipette catchers are formed at inlet and outlet openings of the flow channel. The fluid feeding apparatus comprises a movable pipette head having a couple of pipettes, a head moving mechanism and pumps for sucking and ejecting the fluid through the pipettes. To inject the fluid into the flow channel, ends of the pipettes are pressed onto the pipette catchers. The pipette catchers are formed from a soft material, so that they are deformed resiliently when the ends of the pipettes are pressed onto the pipette catchers, thereby ensuring water-tightness between the pipettes and the flow channel, without the need for fitting the pipettes in the inlet and outlet openings.

15 Claims, 7 Drawing Sheets

FLUID FEEDING SYSTEM, FLUID FEEDING METHOD AND FLOW CHANNEL UNIT

BACKGROUND OF THE INVENTION

The present invention relates to a fluid feeding system using pipettes for feeding sample fluids into a flow channel, and a fluid feeding method for this system. The present invention relates also to a flow channel unit for use in the fluid feeding system.

BACKGROUND OF THE INVENTION

An assay apparatus utilizing attenuated total reflection has been known as a device for assaying reactions of samples, for example, for the purpose of studying interaction of protein, DNA and various biochemical materials, or screening drugs.

A surface plasmon resonance (SPR) sensor is known as such an assay apparatus that utilizes attenuated total reflection. Surface plasmon is a term to mean a compressional wave of free electrons, which moves on the surface of a metal and is caused by mass oscillation of the free electrons inside the metal.

For example, Japanese Patent No. 3294605 discloses an SPR assay apparatus which adopts Kretschmann configuration, wherein a sensor surface is provided as an obverse surface of a meta film formed on a transparent dielectric material, hereinafter called a prism. A sample is reacted on this sensor surface, and thereafter, the metal film is illuminated from the back through the prism in a manner conditioned for total reflection, to measure the reflected light.

Although the light projected onto the metal film is conditioned for total reflection, a small component of the light is not reflected but passes through the metal film and penetrates to the sensor surface. The penetrating light component is called an evanescent wave. When the frequency of the evanescent wave coincides with that of the surface plasmon, surface plasmon resonance (SPR) occurs, which attenuates the intensity of the reflected light remarkably. The incident angle of the attenuating light component, that is called resonance angle, varies depending upon the refraction index on the metal film. So the SPR assay apparatus detects the resonance angle of the reflected light from the metal film, to measure the degree of reaction of the sample on the sensor surface.

For the purpose of preventing modification or deactivation due to drying, the biological sample, such as protein or DNA, is often dissolved in a solvent, to be handled as a sample fluid, wherein examples of the solvents include physiological saline water, pure water, liquid buffers and the like. The above-mentioned prior art discloses the assay apparatus for analyzing interaction of the sample, and the assay apparatus has a flow channel for flowing a sample fluid on a sensor surface. The flow channel and the prism are placed on an assay stage that is built in the apparatus. Specifically, a sensor unit chip consisting of a metal film formed on a glass support is positioned on the assay stage for the above-described measuring step.

According to the above prior art, the sample fluid is fed from a fluid container to the flow channel through a tube that is connected to a pump and valves. There is a problem in this configuration that the sample can adhere to the interior of the tube and mix with another sample fluid that flows through the tube afterward. Such a problem is called contamination.

To solve this problem, an SPR assay apparatus has been suggested, which uses pipettes for feeding a fluid, such as a sample fluid, from a container to a flow channel. The pipette consists of a pipette tip and a pipette head holding the pipette tip removably. The pipette tip is of a substantially conical-tube shape, and has a small hole at its end. In this SPR assay apparatus, each time a different fluid is to be fed, the pipette tip is changed to prevent the contamination of the fluid as being fed to the flow channel.

Besides using the pipettes, the just-mentioned assay apparatus uses a sensor unit that consists of a flow channel block having a flow channel formed therein, a prism having a metal film formed on its top surface, and a holding member. The holding member holds the flow channel member and the prism such that a bottom surface of the flow channel member is put on the top surface of the prism, i.e., the flow channel is opposed to the metal film. The flow channel is a substantially U-shaped tube formed by hollowing out the flow channel member. Opposite ends of the flow channel are exposed on the top surface of the flow channel member. To feed the fluid into the flow channel, the pipette tip is inserted in the ends of the flow channel, and the fluid is dispensed from the pipette. The flow channel member is formed from a soft elastic material, so that the flow channel member is resiliently deformed into tight contact with the prism, when they are pressed together by the holding member. Thereby, the flow channel gets highly water-tight.

However, the flow channel formed from the elastic material has a problem that the flow channel can be deformed by the inserted pipette tip or the depth of insertion of the pipette tip can vary, which results in changing the volume of the flow channel. If the volume of the flow channel varies, the flow rate of the fluid varies, so the fluid can overflow or different kinds of fluids can mix in the flow channel. The movement of the pipette into and out of the flow channel vibrates the fluid to wave in the flow channel, and can cause a measurement error if the fluid waves before the measurement. Besides that, the pipette tip can fit in the flow channel so tightly that it comes off the pipette head as the pipette is pulled out from the flow channel. Moreover, the repetitive insertion and removal of the pipette can decay the flow channel member and cause clogging of the flow channel.

Thus, the insertion of the pipette in the flow channel causes various troubles. When the pipette tip accidentally separates from the pipette head or the flow channel is clogged, the operation of the assay apparatus should be interrupted in order to deal with the trouble. Since the volume variation of the flow channel can cause measurement errors, the above-described assaying method is not sufficiently stable in view of the performance and the accuracy as well.

SUMMARY OF THE INVENTION

In view of the foregoing problems, an object of the present invention is to provide a fluid feeding system consisting of a fluid feeding apparatus and a flow channel unit, which achieves sufficient stability in performance and accuracy.

Another object of the present invention is to provide a fluid feeding method for this system, and a flow channel unit for use in the fluid feeding system.

In order to achieve the above and other objects, the present invention suggests a fluid feeding system wherein a flow channel unit includes at least a flow channel for feeding a sample fluid containing a sample to a sensor surface for detecting reaction of the sample, an inlet opening for introducing the sample fluid into the flow channel, an outlet opening for draining the sample fluid out of the flow channel, and pipette catchers formed at the inlet and outlet openings. On the other hand, a fluid feeding apparatus includes a pipette head having a couple of pipettes for sucking and ejecting the sample fluid, a device for moving the pipette head to the flow channel unit as positioned removably on a designated stage, and pressing ends of the pipettes onto the pipette catchers, to inject the sample fluid into the flow channel, wherein either the ends of the pipettes or the pipette catchers are formed from a soft material so as to be deformed resiliently when the ends of the pipettes are pressed onto the pipette catchers.

According to a preferred embodiment, the pipette catchers are formed from the soft material, whereas a boss is formed on the end of each of the pipettes such that the boss is pressed onto the pipette catcher. It is preferable to provide each of the pipette catchers with a recess for fitting the boss when the end of the pipette is pressed onto the pipette catcher.

According to another embodiment, each of the pipette catchers is formed from the soft material, and has a boss that is depressed as the end of the pipette is pressed onto the pipette catcher.

The pipette catcher may be formed from the soft material integrally with rigid body parts of the flow channel unit, which are formed from a rigid material, by two-color molding.

According to another preferred embodiment, the end of the pipette is formed from the soft material, whereas other portion of the pipette is formed from a rigid material integrally with the pipette end by two-color molding.

It is preferable to provided the fluid feeding apparatus with a device for controlling pressure applied from the ends of the pipettes onto the pipette catchers.

According to the present invention, a fluid feeding method for feeding a fluid to a flow channel by use of pipettes, includes the following steps: positioning a flow channel unit on a stage, the flow channel unit comprising the flow channel, an inlet opening for introducing the fluid into the flow channel, an outlet opening for draining the fluid out of the flow channel, and pipette catchers formed at the inlet and outlet openings; moving a pipette head to the flow channel unit as positioned on the stage, the pipette head having a couple of pipettes for sucking and ejecting the fluid; pressing ends of the pipettes onto the pipette catchers, wherein either the ends of the pipettes or the pipette catchers are formed from a soft material so as to be deformed resiliently according to a pressure applied thereto; and injecting the fluid into the flow channel through the pipettes while the ends of the pipettes being pressed onto the pipette catchers.

A flow channel unit of the present invention includes at least a flow channel for feeding a sample fluid containing a sample to a sensor surface for detecting reaction of the sample, an inlet opening for introducing the sample fluid into the flow channel, an outlet opening for draining the sample fluid out of the flow channel, and pipette catchers formed at the inlet and outlet openings, for catching ends of pipettes while the sample fluid is being injected into the flow channel through the pipettes, wherein the pipette catchers are formed from a soft material so as to be deformed resiliently when the ends of the pipettes are pressed onto the pipette catchers.

According to the present invention, either the pipette catchers or the ends of the pipettes are formed from the soft material so as to be deformed resiliently when the ends of the pipettes are pressed onto the pipette catchers, the water-tightness between the pipettes and the flow channel is ensured. Because the ends of the pipettes are just pressed onto the pipette catchers, without being fitted in the inlet and outlet opening, the flow channel is kept at a constant volume, and the removal of the pipettes from the flow channel does not cause waving of the liquid in the flow channel nor accidental separation of the pipettes from the pipette head. Moreover, the present invention prevents decay of the flow channel member and clogging of the flow channel as well, which would be caused by the repetitive insertion and removal of the pipettes.

BRIEF DESCRIPTION OF THE DRAWINGS

The above objects and advantages of the present invention will become more apparent from the following detailed description when read in connection with the accompanying drawings, in which same reference numerals designate same or equivalent elements throughout the several views.

DETAILED DESCRIPTION OF THE PREFERRED EMBODIMENTS

Figure 1:
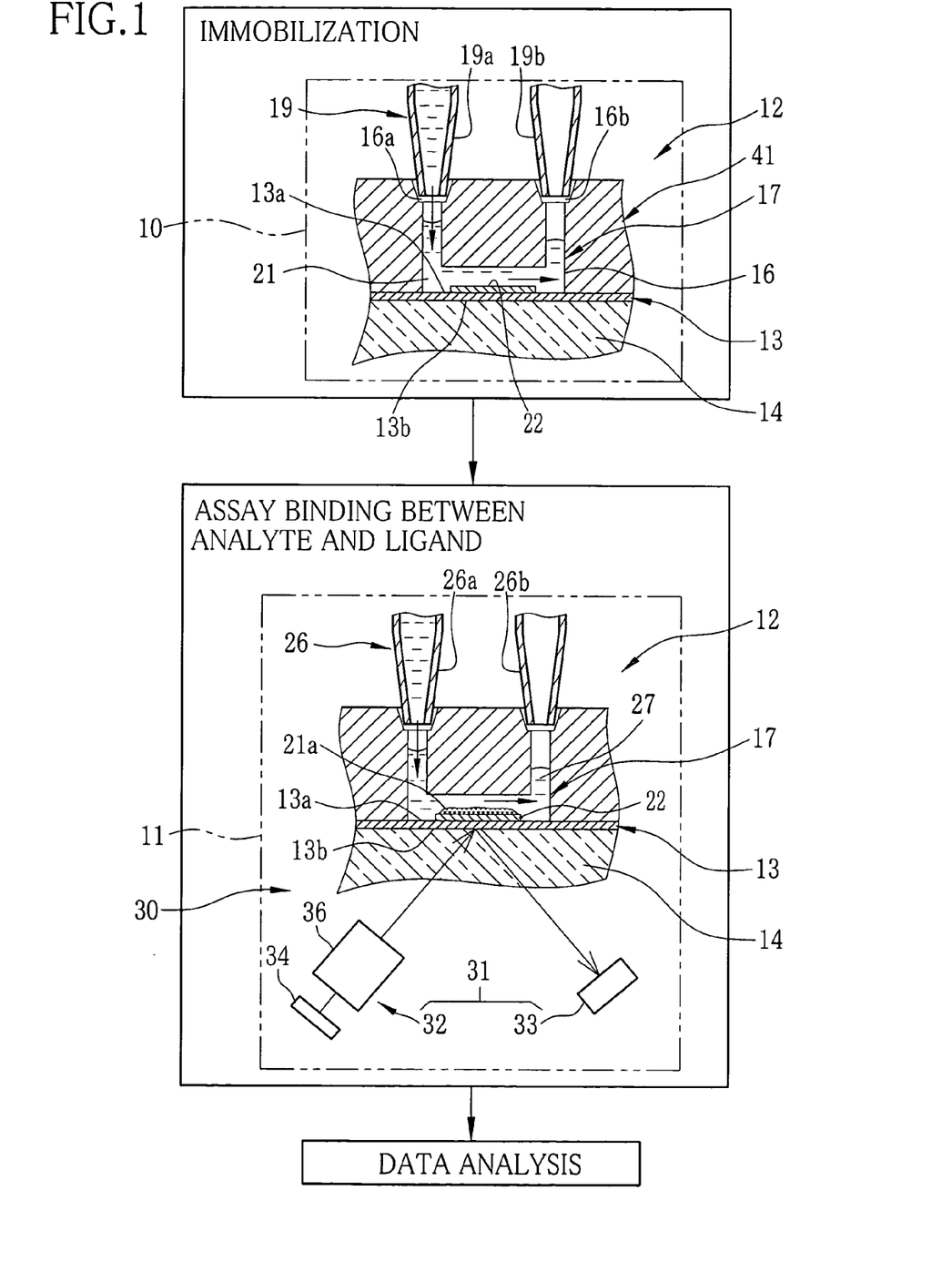
FIG. 1 is an explanatory diagram illustrating a surface plasmon resonance assay method.

As shown in FIG. 1, a measuring or assaying method utilizing SPR (surface plasmon resonance) mainly comprises three processes which are an immobilizing process, an assay process and a data analyzing process. An SPR assay apparatus is constituted of an immobilizing device 10 for the immobilizing process, an assay device 11 for the assay process, and a data analyzer for analyzing data obtained through the assay device 11.

A sensor unit 12 constituting a surface plasmon resonance (SPR) sensor is used for the assay process. The sensor unit 12 includes a metal film 13, a prism 14 and a flow channel member 41. A first surface of the metal film 13 is a sensor surface 13a where the surface plasmon resonance occurs. The prism 14 is joined to a light incident surface 13b that is an opposite surface of the metal film 13 to the sensor surface 13a. The flow channel member 41 is opposed to the sensor surface 13a, and has a flow channel 16 for conducting a fluid such as ligand or analyte through it.

An example of material for the metal film 13 is gold or silver. A thickness of the metal film 13 is, for example, 50 nm. The thickness can be changed appropriately according to the material of the metal film 13, the emission wavelength of light to be applied to the metal film 13, and other factors. The prism 14 is a transparent dielectric material, atop which the metal film 13 is formed. The prism 14 is an optical element for condensing light toward the light incident surface 13b, satisfying conditions for the total reflection. The flow channel 16 is a fluid conductor tube that is curved substantially into a U-shape, and has an inlet opening 16a for letting a fluid into the flow channel 16 and an outlet opening 16b for letting the fluid out of the flow channel 16. For example, the flow channel 16 has a diameter of approximately 1 mm, and an interval between the inlet opening 16a and the outlet opening 16b is approximately 10 mm.

The flow channel 16 has an open bottom, which is closed tightly as being covered with the sensor surface 13a. The flow channel 16 and the sensor surface 13a constitute a sensor cell 17. The sensor unit 12 is provided with a plurality of these sensor cells 17, as will be described later in detail with reference to FIG. 3.

The immobilizing process is a process of immobilizing or fixing ligand on the sensor surface 13a. For this process, the sensor unit 12 is set in the immobilizing device 10. The immobilizing device 10 is provided with a pipette couple 19 that consists of a couple of pipettes 19a and 19b. The pipette 19a is for dispensing the fluid into the flow channel 16, whereas the pipette 19b is for sucking the fluid out of the flow channel 16. While the pipette 19a is dispensing a liquid, the pipette 19b is sucking the liquid out of the flow channel 16 cooperatively. In the immobilizing process, the pipette couple 19 injects a ligand solution 21, a solution of ligand dissolved in a solvent, through the inlet opening 16a. A linker film 22 is formed on a central area of the sensor surface 13a previously in the manufacturing process of the sensor unit 12. The linker film 22 is for binding the ligand. As the linker film 22 is a basis for immobilizing the ligand, a material for the linker film 22 is determined by the kind of the ligand to immobilize.

As a pre-treatment before the introduction of the ligand solution 21 for immobilizing the ligand, a liquid buffer for immobilization is fed to the linker film 22 in order to wet the linker film 22, and thereafter, an activation process is executed to promote binding of the ligand to the linker film 22. For example, according to the amine coupling method, the linker film 22 is made of carboxy methyl dextran, to bind amino groups contained in the ligand to the dextran directly by covalent binding. In that case, as a liquid for the activation, a mixture of N'-(3-dimethylaminopropyl)carbodiimide hydrochloride (EDC) and N-hydroxy imide succinate (NHS) is introduced. After the activation of the linker film 22, the liquid buffer for immobilization is introduced to wash out the flow channel 16.

For use as the liquid buffer for immobilization, and as solvent or diluent for the ligand solution 21, various liquids are available, e.g., many kinds of buffering liquids, physiological saline water and other aqueous solutions of physiological salts, and pure water. The types and pH values of these solutions, and the types and density of substances to be mixed are determined appropriately according to the type of the ligand. Where the ligand is a biomaterial, it is ordinal to use physiological saline water of which pH value is neutralized. In the above-described amine coupling method, because the linker film 22 is electrified negatively by the carboxy methyl dextran, a solution that electrifies protein positively is used as the liquid buffer, to facilitate binding to the negative linker film 22. An example of such a solution is phosphate buffered saline (PBS) solution having strong operation of buffer and containing phosphate salt at such a high density that is not physiological.

After the activation and washing, the ligand solution 21 is injected into the sensor cells 17 for the immobilizing process of the ligand. The ligand 21a diffused in the injected ligand solution 21 gradually comes near to and is bound to the linker film 22. Thus, the ligand 21a is fixed on the sensor surface 13a. The immobilization process generally requires approximately one hour, during which the sensor unit 12 is preserved in an environment conditioned suitably, for example at a conditioned temperature. In the course of the immobilization, the ligand solution 21 in the flow channel 16 may be left to stand in a stationary state. However, it is preferable to stir the ligand solution 21 to flow in the flow channel 16, because the stirring or turbulent flow promotes binding of the ligand 21a to the linker film 22, and thus raises the immobilized amount of the ligand 21a.

When the immobilization of the ligand 21a on the sensor surface 13a is accomplished, then the ligand solution 21 is discharged from the flow channel 16. After this, the sensor surface 13a is washed by feeding washing liquid into the flow channel 16. If necessary, a blocking step is executed after the washing step, wherein a blocking liquid is introduced into the flow channel 16, to inactivate those reaction groups which remain unbound with the ligand. A preferable example of the blocking liquid is ethanol amine hydrochloride. After the blocking, the flow channel 16 is washed again. Then a liquid for preventing drying the sensor surface 13a is injected into the flow channel 16, in order to preserve the sensor unit 12 until the assay process, with the sensor surface 13a soaked in the liquid.

For the assay process, the sensor unit 12 is set in the assay device 11. A pipette couple 26 is disposed in the assay device 11 in the same manner as the pipette couple 19 of the immobilizing device 10. The pipette couple 26 introduces liquid of several types into the flow channel 16 through the inlet opening 16a. At first, liquid buffer for assay is introduced into the flow channel 16. After this, an analyte solution 27, a solution of an analyte dissolved in a solvent, is introduced into the flow channel 16. Thereafter, the liquid buffer for assay is introduced again. Note that the flow channel 16 may be washed before initially introducing the liquid buffer for assay. Immediately after the liquid buffer for assay is introduced for the first time, data starts being read, in order to detect a reference signal level. The data reading is continued until the liquid buffer for assay is introduced at the second time after the analyte solution 27. Thus, the SPR signal is measured first to detect the reference level, and then to detect reaction or binding between the analyte and the ligand, and dissociation between the analyte and ligand as a result of the second introduction of the liquid buffer for assay.

For use as the liquid buffer for assay, and as solvent or diluent for the analyte solution 27, various liquids are available, e.g., many kinds of buffering liquids, physiological saline water and other aqueous solutions of physiological salts, and pure water. The types and pH values of these solutions, and the types and density of substances to be mixed are determined appropriately according to the type of the analyte. To facilitate dissolving of the analyte, dimethyl sulfo-oxide (DMSO) can be added to the physiological saline water. The DMSO has a large influence on a level of an output signal. As described above, since the liquid buffer for assay is used for detecting the reference level of the signal, it is preferable to use such a liquid buffer for assay that contains DMSO at a density approximately equal to that of the solvent for the analyte, if the solvent contains DMSO.

Note that the analyte solution 27 is often kept preserved for a long time, for example one year. In that case, the DMSO density of the analyte solution 27 can differ from its initial level because of the change with time. To achieve the assay with high precision, the difference in the DMSO density is estimated based on the reference signal level obtained when the analyte solution 27 is introduced, and measured data is corrected based on the DMSO density difference (DMSO density correction).

A reference signal (ref-signal) is the SPR signal obtained by measuring a reference region on the sensor surface 13a, the reference region having no ligand immobilized. The reference signal is used for comparison and reference with a measured signal (act-signal) of an assay region on which the ligand is immobilized to react on the analyte. For the assay, both of the measured signal and reference signal are detected and evaluated. For example, a difference between these SPR signals is calculated and used as measured data for analysis. This method is effective to cancel electric noise caused by external irregularities, such as individual specificity of sensor cells, temperature changes of the liquid, and the like, so a signal with a high S/N ratio can be obtained.

Correction data for the DMSO density correction may be obtained before the analyte solution 27 is introduced. Specifically, liquid buffers with different DMSO densities for measurement are introduced into the sensor cells 17. The correction data is obtained based on the variations in levels of the ref-signal and the act-signal, which accord to the differences in the DMSO density.

A photometric system 31 consisting of an illuminator 32 and a photo detector 33 is fixedly positioned on an assay stage 30 of the assay device 11. The assay stage 30 has a not-shown stage base, on which the illuminator 32 and the photo detector 33 are fixedly positioned at such angles that satisfy the conditions for total reflection, and the sensor unit 12 is positioned on an optical path of the illuminator 32. As described above, the reaction between the ligand and analyte can be recognized as a change in resonance angle, the incident angle of light projected toward the light incident surface 13b. So the illuminator 32 projects light to the light incident surface 13b at different incident angles satisfying the conditions for total reflection. For example, the illuminator 32 is constituted of a light source 34 and an illuminating optical system 36, which includes a condensing lens, a diffusing plate and a polarizing plate. Positions and installation angles of these elements are determined such that the light incident angle satisfies the condition for the total reflection.

The light source 34 may be a light emitting element, such as a light emitting diode (LED), a laser diode (LD), a super luminescent diode (SLD). A single element is used as the light source 34 to emit light toward one sensor cell 17. To measure a plurality of sensor cells 17 at once, the light from the single light source may be split into a plurality of light beams toward the sensor cells 17, or it is possible to arrange a corresponding number of light emitting elements in one-to-one relationship. The diffusing plate diffuses light from the light source 34, to suppresses irregularity in the light amount in the light emission surface. The polarizing plate allows passage of only p-polarized light components of the projected light, the p-polarized light creating the surface plasmon resonance. In a case where the light source 34 emits rays of the same polarizing direction, like where a laser diode is used as the light source 34, the polarizing plate is unnecessary. However, even where the light source 34 emits rays in the same polarizing direction, if the polarizing directions of the rays become unequal as the rays pass through the diffusing plate, the polarizing plate is used for aligning the polarizing direction. The light obtained through the diffusion and the polarization is condensed by a condensing lens, and directed to the prism 14. In this way, the light can fall on the light incident surface 13b at various incident angles, without irregularity in the intensity.

The photo detector 33 receives light reflected by the light incident surface 13b, and detects intensity of the light. Rays of light are incident upon the light incident surface 13b at various angles. According to the various incident angles, light is reflected by the light incident surface 13b at various angles of reflection, so the photo detector 33 receives light at various angles. If any change occurs in the medium on the sensor surface 13a, the refraction index changes, so the incident angle at which the intensity of the reflected light attenuates, i.e. the resonance angle causing the SPR, changes too. When the analyte flows on the sensor surface 13a, the refraction index on the sensor surface 13a changes according to interaction between the analyte and the ligand, so the resonance angle changes accordingly.

An example of the photo detector 33 is a CCD area sensor or a photo diode array. The photo detector 33 receives the reflected light as reflected at various reflection angles from the light incident surface 13b, and converts the reflected light photoelectrically into the SPR signals. The interaction between the ligand and the analyte comes out as a shift of the attenuating position of the light in a photo receiving surface of the photo detector 33. After the contact of the analyte with the ligand, the refraction index on the sensor surface 13a and thus the resonance angle for generating surface plasmon resonance change from before. As the reaction starts upon contact of the analyte with the ligand, the resonance angle begin to change, so the attenuating position of the reflected light in the photo receiving surface begin to shift. Thus, the photo detector 33 outputs the SPR signal representative of the state of the interaction to the data analyzer. In the data analyzing process, the SPR signal from the assay device 11 is analyzed to analyze characteristics of the analyte.

Figure 2:
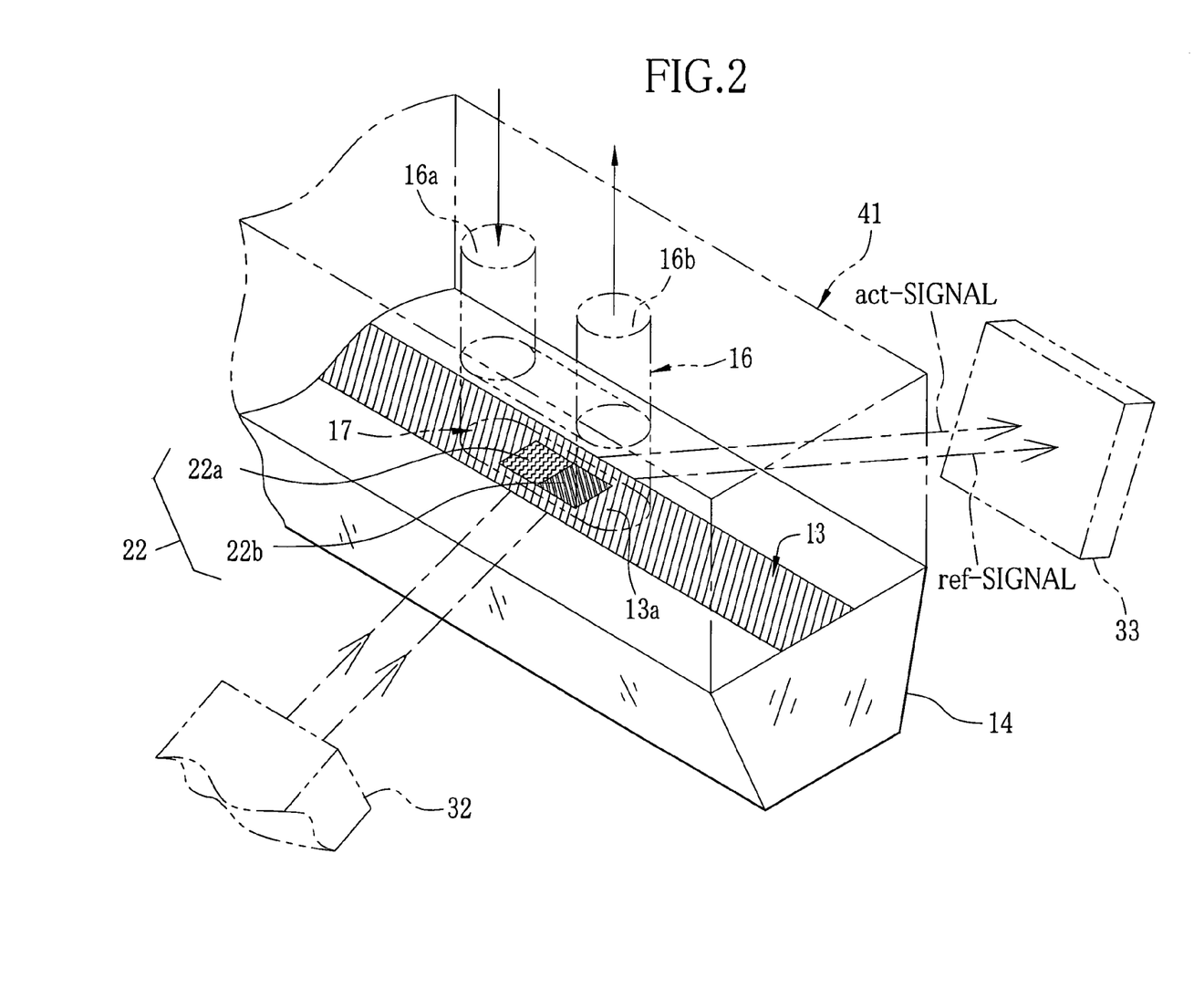
FIG. 2 a perspective view illustrating a sensor cell of a sensor unit in association with a photometric system of an assay device.

Note that FIG. 1 illustrates the illuminator 32 and the photo detector 33 as positioned such that the light projected onto and reflected from the light incident surface 13b travels along the liquid flowing direction through the flow channel, for convenience sake. However, the illuminator 32 and the photo detector 33 are actually position in a manner as shown in FIG. 2, such that the light is projected and reflected in a direction orthogonal to the liquid flowing direction. Of course, the photometric system 31 may be arranged in the manner as shown in FIG. 1.

As shown in FIG. 2, the assay region 22a and the reference region 22b are formed on the linker film 22. The assay region 22a has the ligand immobilized, so the reaction between the ligand and the analyte occurs in this region 22a. The reference region 22b does not have the ligand immobilized, and is used to obtain the reference signal that is used for signal measurement in the assay region 22a. The reference region 22b is formed in the course of manufacturing the linker film 22. For example, approximately a half of the entire area of the linker film 22 is subjected to a surface processing for deactivating those binding groups which will be bound to the ligand. Thus, the processed half of the linker film 22 becomes the reference region 22b, while the remaining half of the linker film 22 becomes the assay region 22a.

The SPR signal obtained by measuring the assay region 22a is output as an act-signal from the photo detector 33, whereas the SPR signal obtained by measuring the reference region 22b is output as a ref-signal from the photo detector 33. The act-signal and the ref-signal are measured simultaneously during the period starting from the detection of a reference level through the detection of the binding reaction to the detection of the dissociation. Data analysis is effected based on a difference or a ratio between the act-signal and ref-signal. For example, the data analyzer obtains data of a finite difference between the act-signal and ref-signal, and analyzes various items based on the finite difference. This makes it possible to cancel electric noise caused by external irregularities, such as individual specificity of sensor units or sensor cells, mechanical variations in the apparatuses, temperature changes of the liquid, and the like. Thus, a highly accurate measurement or assay is achieved.

The illuminator 32 and the photo detector 33 are so constructed as to measure the act-signal and the ref-signal in two channels. For example, the illuminator 32 has a light emitting element and a reflection mirror for splitting the light from the light emitting element into plural light beams which are directed respectively to the assay region 22a and the reference region 22b. The photo detector 33 is constituted of a plurality of arrays of photo diodes, to receive reflected light beams from the respective regions.

If a CCD area sensor is used as the photo detector 33, the reflected light beams of the dual channels received at the same time can be discriminated between the act-signal and the ref-signal through some image processing. However, such image processing might be difficult. In that case, it is possible to receive the optical signals of the respective channels at slightly different timings by shifting the timing of incidence of the light beams on the assay region 22a slightly from that on the reference region 22b. As an example for differentiating the timing of incidence, a rotary disk having two holes is disposed on the light paths. The holes are positioned at 180 degrees from each other in the rotational angle, and their radial positions or distances from the rotary center differ from each other by an amount corresponding to an interval between the assay and reference regions 22a and 22b. When one of the holes enters the light path, the light travels to the assay region 22a. When the other hole enters the light path, the light travels to the reference region 22b. Thus, the rotation of the disc shifts the timing of incidence of one channel from that of the other channel disk.

Figure 3:
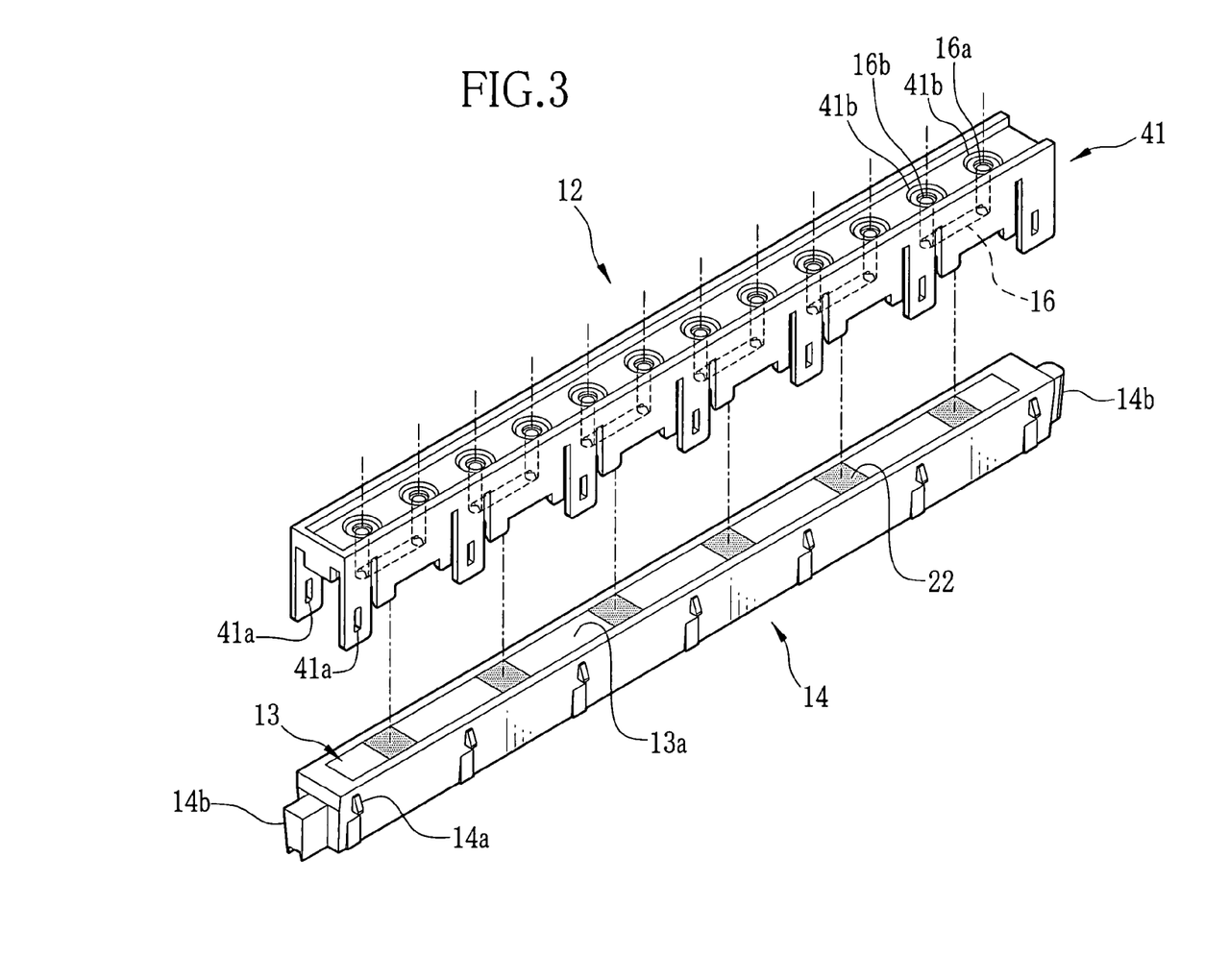
FIG. 3 is an exploded perspective illustrating the sensor unit in which a flow channel device is included.

FIG. 3 shows an exploded perspective view of the sensor unit 12. The sensor unit 12 includes the prism 14 and the flow channel member 41. The prism 14 has the metal film 13 formed on its top surface. The flow channel member 41 has six flow channels 16 formed therein, and is mounted on the prism 41 with the flow channels 16 opposed to the metal film 13a.

The metal film 13 is deposited on the prism 14 by vapor deposition. The metal film 13 is formed into a rectangular strip that extend to oppose to the flow channels 16 of the flow channel member 41. Also, six linker films 22 are formed on an upper face or the sensor surface 13a of the metal film 13, in regions corresponding to the six flow channels 16. The prism 14 has fastening claws 14a formed on its opposite longer sides. As the fastening claws 14a are engaged in fastening holes 41a of the flow channel member 41, the flow channel member 41 is held on the prism 14, while keeping the bottom surface of the flow channel member 41 in tight contact with the top surface of the prism 14.

Retaining projections 14b are formed on opposite ends or shorter sides of the prism 14. Although it is omitted from the drawings, a sensor holder is used to hold the sensor units 12 to be set in the immobilizing device 10 or the assay device 11. The retaining projections 14b are formed to fit in slits of the sensor holder, for positioning the sensor unit 12 regularly in the sensor holder 52.

Note that the prism 14 may be formed from an optical glass, such as borosilicate crown (BK7) glass, barium crown (Bak4) glass and the like, or an optical plastic material, such as polymethyl methacrylate (PMMA), polycarbonate (PC), amorphous polyolefin (APO) and the like.

The flow channel member 41 is elongated in one direction, and the six flow channels 16 are arranged along the length. The inlet openings 16a and the outlet openings 16b of the respective low channels 16 are exposed on the top surface of the flow channel member 41. The entrance and outlet openings 16a and 16b are recessed from the top surface of the flow channel member 41, and have funnel-shaped rims 41b that let the liquid leaking from the pipette flow into the flow channel 16. Note that the number of the flow channels 16 and the associated linker films 22, i.e. the number of sensor cells 17 provided in one sensor unit 12, is not to be limited to six, but may be less than or more than six.

Figure 4:
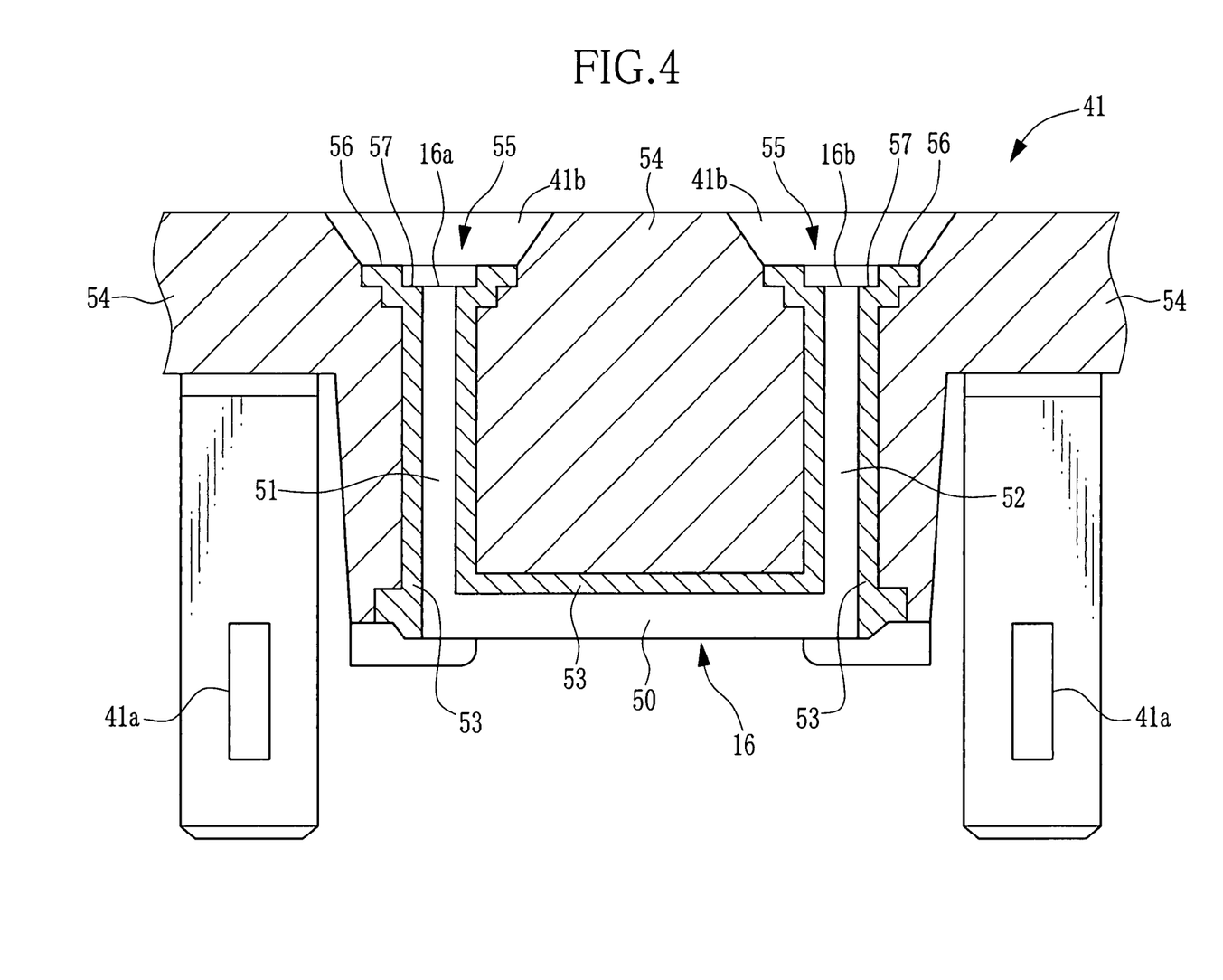
FIG. 4 is a cross section illustrating a flow channel of the flow channel device.

FIG. 4 shows a sectional contour of the flow channel 16 of the flow channel member 41. The flow channel 16 consists of a groove section 50, an injecting section 51 and a draining section 52. The groove section 50 is a slit formed in the bottom surface of the flow channel member 41, and is closed when the flow channel member 41 comes into contact with the top surface of the prism 14. The injecting section 51 and the draining section 52 are through-holes extending vertically from opposite ends of the groove section 50 to the entrance and outlet openings 16a and 16b respectively.

The flow channel member 41 includes elastic soft body parts 53 and rigid body parts 54 that are harder than the soft body parts 53. The soft body parts 53 constitute the entire inner walls of the flow channels 16, whereas the rigid body parts 54 constitute other portions including the fastening claws 41a. The soft body parts 53 and the rigid body parts 54 are formed integrally by the two color molding or double molding, in which two different materials are molded in combination in the same mold die. In the groove sections 50 of the flow channels 16, the soft body parts 53 protrude slightly downward from the bottom surface of the rigid body parts 54, so that the soft body parts 53 resiliently deform to close clearances between the metal film 13 and the flow channel member 41 as the flow channel member 41 is pressed onto the top side of the prism 14. Thus, the protruding ends of the soft body parts 53 seal the joint between the flow channel member 41 and the prim 14, to close the open bottoms of the flow channels 16 water-tightly. The soft body parts 53 preferably have a thickness of 0.1 mm to 1.0 mm. With the thickness of less than 0.1 mm, it is difficult to obtain satisfactory water-tightness by the elastic deformation of the soft body parts 53. With the thickness of more than 1.0 mm, the elastic deformation of the soft body parts 53 may cause deviation of the flow channels 16 from the linker films 22. The amount of protrusion of the soft body parts 53 from the bottom surface is preferably around 0.1 mm in consideration of its elasticity.

Since the soft body parts 53 constitutes the inner walls of the flow channels 16, they get contact with the fluid flowing in the flow channel 16. For the sake of preventing adsorption of samples dissolved in the fluid, such as the ligand and the analyte, it is preferable to form the soft body parts 53 from a material with small non-specific adsorption. As a known example of soft elastic materials with small non specific adsorption, which are preferable for the soft body parts 53, is amorphous polyolefin elastomer. As a material for the rigid body parts 54 to be formed integrally with the soft body parts 53, crystalline polyolefin, such as polypropylene, is usable.

At upper ends of the injecting section 51 and the draining section 52, pipette catchers 55 are formed around the inlet opening 16a and the outlet opening 16b. The immobilizing device 10 and the assay device 11 inject and discharge the liquid into and out of the flow channel 16 while fitting the ends of the pipette couple 19 or 26 in the inlet opening 16a and the outlet opening 16b. The pipette catcher 55 has a circular catching surface 56 on which the pipette is pressed, and a stepped recess 57 formed around inner periphery of the catching surface 56. Each pipette catcher 55 is formed as an extension of the soft body parts 53 that constitute the inner wall of the flow channel 16. The pipette catchers 55 are elastically deformed by the pressure applied from the pipettes, thereby reinforcing the water-tightness during the injection and the draining of the liquid into and out of the flow channel 16. On the other hand, the rigid body parts 54 prevent the flow channels 16 from being deformed by the pressure applied from the pipettes. This ensures transmission of the pressure from the pipettes to the pipette catchers 55, and thus ensure the water-tightness effectively with less pressure.

It is possible to attach an RFID (radio frequency identification) tag, a non-contact IC memory, to the sensor unit 12. For example, an ID number of each individual sensor unit 12 is written on a read-only RFID tag, so that the sensor unit 12 may be identified before each process by reading the ID number. This is effective to prevent such troubles as injection of wrong analyte and confusion of results of the assay, even where a number of sensor units 12 are simultaneously subjected to the immobilization and assay processes. It is possible to use a read-write RFID tag for recording data on the assay, including the kind of immobilized ligand, the time of ligand immobilization, the kind of analyte used as reactant, and the like.

Figure 5:
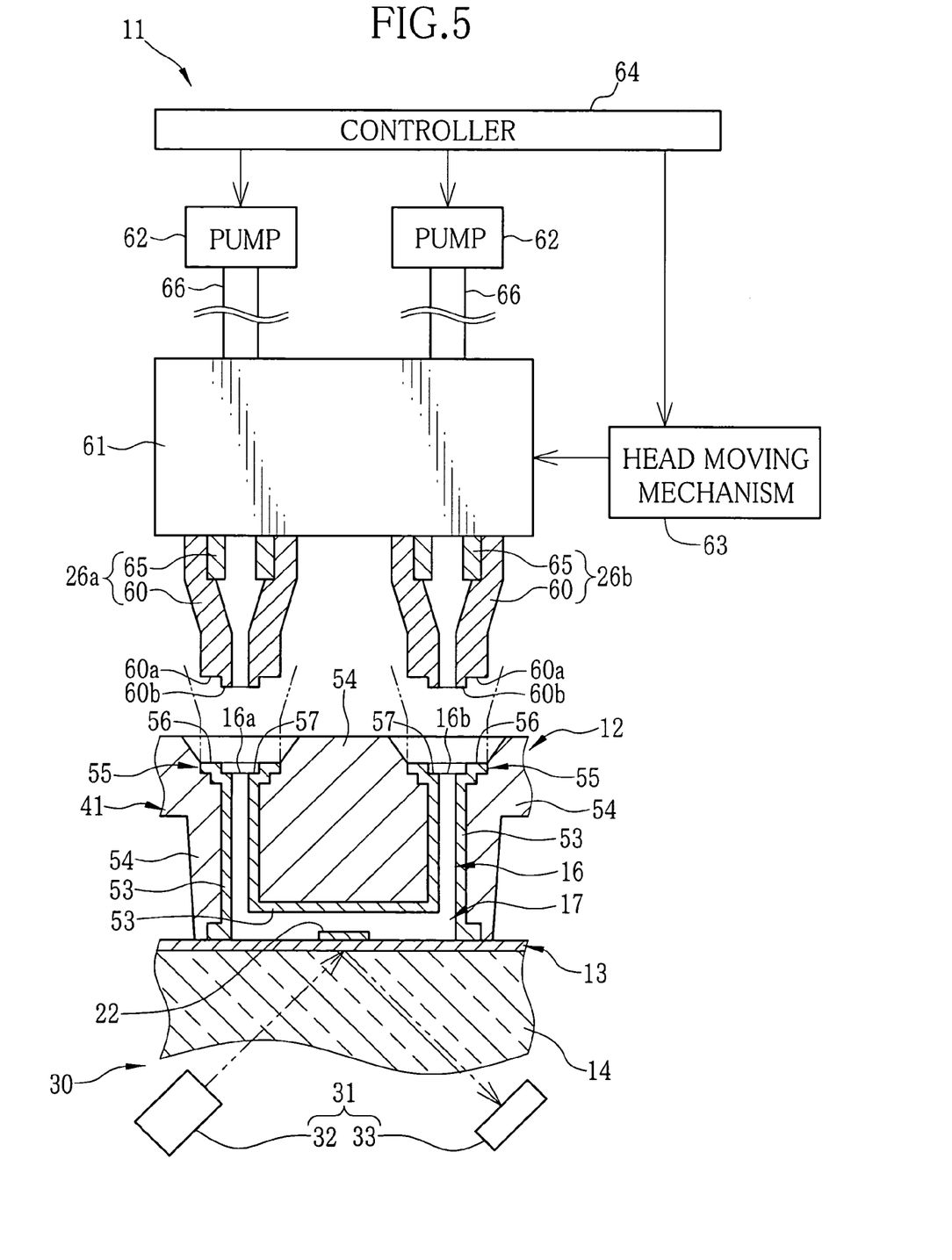
FIG. 5 is a schematic diagram illustrating the structure of the assay device.

FIG. 5 schematically shows the structure of the assay device 11. The assay device 11 has the photometric system 31 consisting of the illuminator 32 and the photo detector 33, the assay stage 30 mounting the photometric system 31 securely and holding the sensor unit 12 removably, a pipette head or dispenser heads 61 for holding the pipette tips 60 removably, pumps 62 for raising or lowering internal pressure of the individual pipette tips 60 to suck and inject a liquid through the pipette tips, a head moving mechanism 63 for moving the pipette heads 61 horizontally in two orthogonal directions as well as vertically, and a controller 64 for general control of the respective components of the assay device 11.

Each pipette head 61 has two cylindrical nozzles 65 that protrude downward. The nozzles 65 have an external diameter that is approximately equal to an internal diameter of the pipette tips 60, so the pipette tips 60 are secured to the pipette head 61 by being mechanically fitted on the nozzles 65. Namely, the respective pipettes 26a and 26b are assembled by fitting the pipette tips 60 on the nozzles 65. The pipette head 61 is further provided with a not-shown release mechanism, which pushes down the pipette tips 60 to detach them from the nozzles 65. As having direct contact with the liquid to dispense, the pipette tips 60 are changed after they dispense one liquid, so as to prevent mixture of different liquids.

The end of the pipette tip 60 has a shape complementary to the pipette catcher 55. That is, the pipette tip 60 has a contact surface 60a that comes into contact with the catching surface 56, and an annular boss 60b that fits in the recess 57. As the boss 60b fits in the recess 57 during the injection and draining of the liquid into and out of the flow channel 16, the water-tightness is improved.

As the respective pumps 62 for the pipettes 26a and 26b, so-called syringe pumps are usable. The syringe pump consists of a cylinder and a piston. The pumps 62 are connected to the nozzles 65 in one-to-one relationship through respective tubes 66 and the pipette head 61. The pump 62 causes the pipette 26a or 26b to suck the liquid by lowering the internal pressure of the tube 66 and the nozzle 65, and also causes the pipette 26a or 26b to eject the liquid as sucked before, by raising the internal pressure of the tube and the nozzle 65.

The controller 64 sends drive signals to the respective pumps 62 through a not-shown pump drivers, to control timing and amount of suction and injection, and other operation of the pumps 62. On feeding a liquid into the flow channel 16, the controller 64 drives the respective pump 92 to cooperate with each other, such that one of the pipettes 26a and 26b ejects the liquid while the other sucks it.

The head moving mechanism 63 may be a well-known mechanism constituted of a conveyer belt, pulleys, a carriage, a motor and other minor components, and carries the pipette head 61 to move left and right, back and forth, as well as up and down, under the control of the controller 64. The assay device 11 is provided with a plurality of liquid preserving sections for preserving different kinds of liquids to dispense, including analyte solutions, liquid buffers for assay and washing liquids, and a pipette tip storage section for storing a plurality of pipette tips 60, though they are omitted from the drawings. The head moving mechanism 63 carries the pipette head 61 to any of the liquid preserving sections, the pipette tip storage section and the sensor units 12 placed in the assay device 11.

Figure 6:
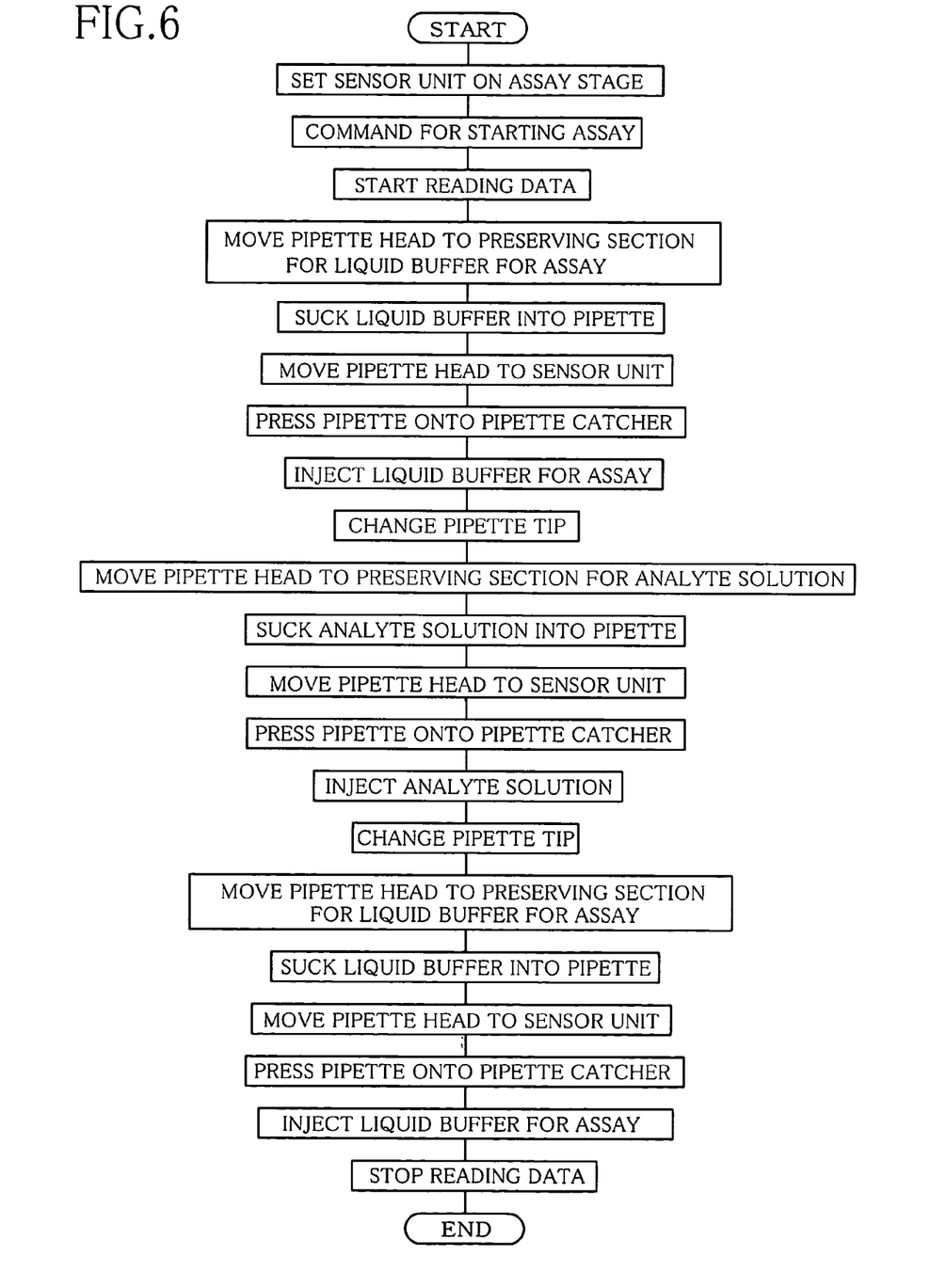
FIG. 6 is a flow chart illustrating a sequence of an assay process in the assay device.

Now the operation of the present invention will be described with reference to the flow chart shown in FIG. 6.

To subject the sensor unit 12 to the assay process, the sensor unit 12 with immobilized ligand is set on the assay stage 30, so as to position the sensor cell 17 in an assay position that is located on the optical path of the illuminator 32. Thereafter, upon the operator entering an assay start command, the assay device 11 starts the assay process. Setting of the sensor unit 12 on the assay stage 30 may be done manually by the operator, or automatically by a well-known mechanism.

Upon the assay start command, the controller 64 drives the photometric system 31 to start data-reading. At the same time, the controller 64 drives the head moving mechanism 63 to move the pipette head 61 to the liquid preserving section where the liquid buffer for assay is preserved. When the pipette head 61 is moved to the liquid preserving section, the controller 64 sends the drive signal to the pump 62 for the pipette 26a, to cause the pipette 26a to suck the liquid buffer for assay.

Thereafter the controller 64 causes the pipette head 61 to move to the sensor unit 12. When the sensor unit 12 comes above the sensor unit 12, the controller 64 drives the head moving mechanism 63 to move the pipette head 61 downward to press the ends of the respective pipettes 26a and 26b onto the pipette catchers 55 of the target sensor cell 17. In that case, the pressure applied from the pipettes 26a and 26b onto the pipette catchers 55 is adjusted by the controller 64 through the head moving mechanism 63. Because the pipette catchers 55 are made of the soft body parts 53, they are deformed elastically according to the pressure applied from the ends of the pipettes 26a and 26b, so the pipettes 26a and 26b are kept joined water-tightly to the flow channel 16. Besides, the end of the pipette tip 60 is shaped complementarily to the shape of the pipette catcher 55, such that the boss 60b is fitted in the recess 57 of the pipette catcher 50 when the pipette tip 60 is pressed onto the pipette catcher 50. So the water-tightness is further improved.

After pressing the pipettes 26a and 26b onto the pipette catchers 55, the controller 64 sends the drive signal to the respective pumps 62, to cause the pipette 26a to eject the previously sucked liquid buffer to inject it into the flow channel 16, and at the same time, cause the pipette 26b to suck the air or previously injected liquid, such as the vapor retardant liquid, out of the flow channel 16. Thus, the pipette couple 26 feeds different kinds of liquids seriatim to the linker film 22, while changing the fluid in the flow channel 16 with new one.

Since the ends of the pipettes 26a and 26b are pressed onto the pipette catchers 55 in the present embodiment, the depth of insertion of the pipettes 26a and 26b into the sensor unit 12 is kept at a constant value. Since the flow channel member 41 is formed from the soft elastic material and the rigid material by two-color molding, the flow channel 16 will not be deformed by the pressure applied from the pipettes. Accordingly, the flow channel 16 is kept at a constant volume, so the liquids may be dispensed by the same amount into the flow channel 16, without flooding from the flow channel 16 or being mixed with each other.

After the liquid buffer for assay is injected into the flow channel 16, the controller 64 carries the pipette head 61 to the pipette tip storage section. For this movement, the pipette head 61 is just moved up to release the pressure on the pipette catchers 55. So the removal of the pipettes 26a and 26b from the sensor unit 12 does not cause waving of the liquid buffer for assay in the flow channel 16, which may affect the data-reading. Also, the removal of the pipettes 26a and 26b does not cause accidental separation of the pipette tip 60 from the nozzle 65. When the pipette head 61 moves in the pipette tip storage section, the pipette tips 60 used for dispensing the liquid buffer for assay are released from the pipette head 61, and unused pipette tips 60 are fit on the nozzles 65. Since the pipette tips 60 are changed this way, the analyte solution to be dispensed next is prevented from being mixed with the liquid buffer for assay that remains in the used pipette tips 60. If the pipette 26b holds any liquid drained from the flow channel 16, the pipette head 61 is moved to a not-shown waste tank, to discharge the liquid from the pipette 26b into the waste tank, before changing the pipette tips 60.

After changing the pipette tips 60, the controller 64 carries the pipette head 61 to the liquid preserving section for the analyte solution, to feed the analyte solution to the flow channel 16 in the same way as for the liquid buffer for assay. Thereafter, in the same way as above, the liquid buffer for assay is fed again into the flow channel 16, for the dissociation. After the dissociation step, the controller 64 stops the data-reading operation of the photometric system 31. Thus, the photometric system 31 measures the SPR signal, starting from the detection of the reference level or base line, through the detection of the reaction or binding process between the analyte and the ligand, to the end of the dissociation of the analyte from the ligand.

A sequence of steps for the assay of one sensor cell 17 are executed in the above described manner. Where the sensor unit 12 includes a plurality of sensor cells 17, like in the present embodiment, the same steps for the assay are executed on the individual sensor cells 17. The assay process for one sensor unit 12 is completed when all of the sensor cells 17 of one sensor unit 12 are subjected to the assay steps.

In the above embodiment, the pipette catchers 55 are formed as the soft body parts 53 to deform elastically upon the pipettes 26a and 26b being pressed on them, whereas the pipette tip 60 has the boss 60b at its end, which is fitted in the recess 57 of each pipette catcher 55. These configurations ensure the water-tightness between the pipette couple 26 and the flow channel 16. However, the present invention is not limited to the above embodiment, but many variations for ensuring the water-tightness are possible.

Figure 7:
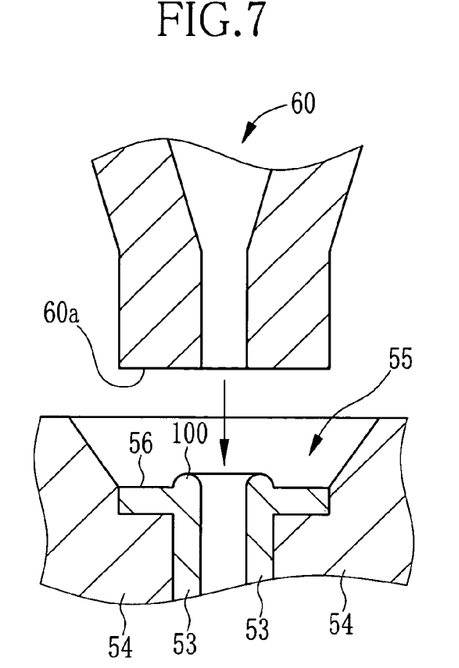
FIG. 7 is a sectional view illustrating a pipette tip and a pipette catcher of a flow channel, according to another embodiment.

For example, as shown in FIG. 7, a pipette catcher 55 may have a boss 100, whereas a pipette tip 60 may merely have a contact surface 60a at its end. The boss 100 is formed as the elastic soft body part 53, so is depressed by the pressure from the contact surface 60a, thereby ensuring the water-tightness between the pipette couple 26 and the flow channel 16.

Figure 8:
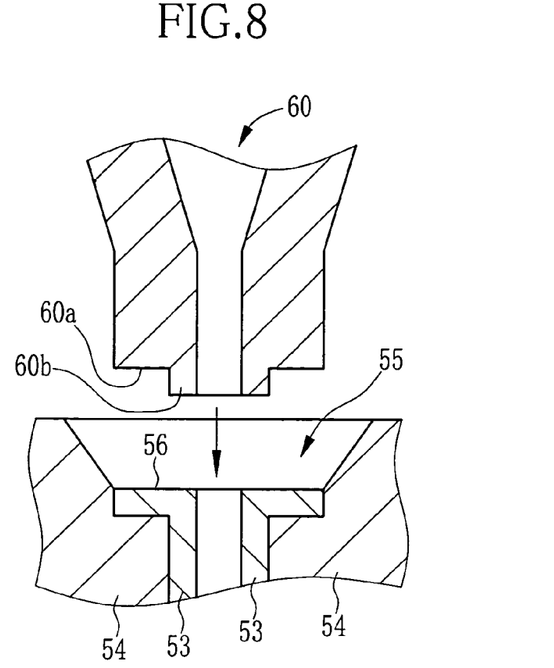
FIG. 8 is a sectional view illustrating a pipette tip and a pipette catcher of a flow channel, according to still another embodiment.
Figure 9:
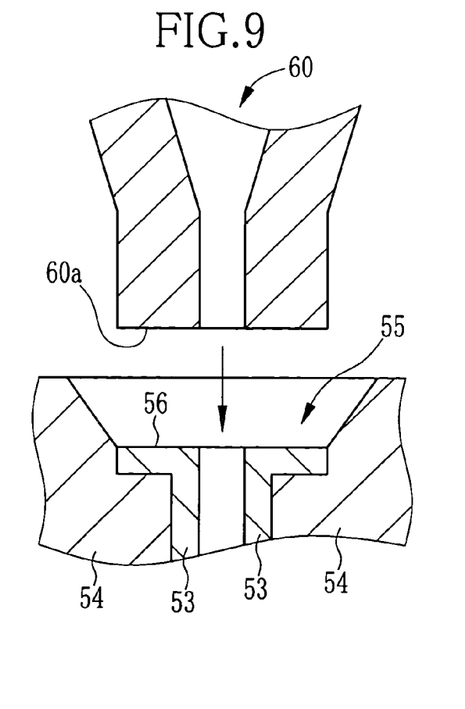
FIG. 9 is a sectional view illustrating another combination of a pipette tip and a pipette catcher.
Figure 10:
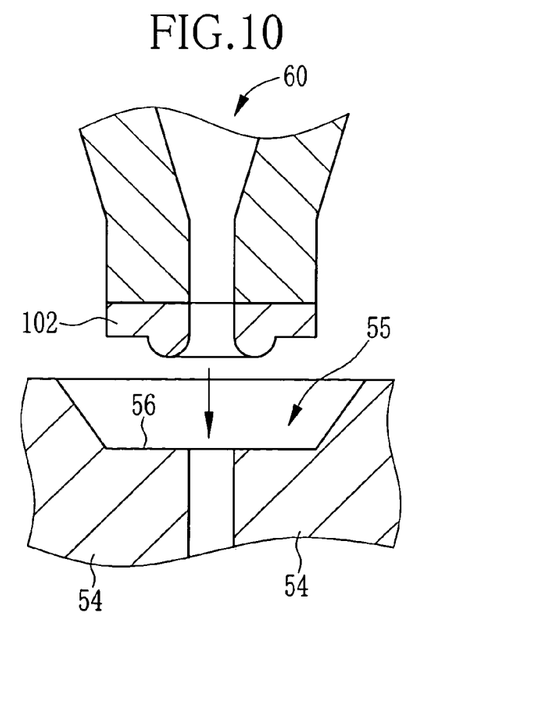
FIG. 10 is a sectional view illustrating a pipette tip and a pipette catcher, according to a further embodiment.

It is possible to form a pipette catcher 55 to have merely a catching surface 56, as shown in FIG. 8. In that case, the water-tightness is ensured by pressing the boss 60b formed on the end of the pipette tip 60 onto the catching surface 56. Even where a pipette catcher 55 and a pipette tip 60 have only a catching surface 56 and a contact surface 60a respectively, as shown in FIG. 9, the water-tightness can be ensured by pressing the contact surface 60a tightly onto the catching surface 56. As shown in FIG. 10, it is also possible to form a pressing portion 102 from a soft elastic material on the end of a pipette tip 60, by two-color molding or the like. In that case, a pipette catcher 55 may be formed as a rigid body part 54. Because the pressing portion 102 is deformed elastically when pressed onto a catching surface 56 of the pipette catcher 55, the pipette tip 60 is joined to the flow channel 16 water-tightly.

Providing the pipette tip 60 with the boss 60b, as shown in FIG. 8, ensures the water-tightness effectively with a smaller pressure, because the pressure is concentrated on the boss 60b. On the other hand, the pipette tip 60 having the contact surface 60a alone, as shown in FIGS. 7 and 9, has such advantages that it is easy to mold, less damages the sensor unit 12, and is improved in durability.

Although the present invention has been described with reference to the assay device 11, the present invention is applicable to the immobilizing device 10. Furthermore, the present invention is applicable to any other liquid feeding systems that use pipettes, such as a pipetting dispenser.

In the above embodiment, the flow channel member 41 is described as a flow channel unit of the invention, but a sensor unit having a prim and a flow channel member as one body may be regarded as a flow channel unit of the invention. Where the flow channel member 41 is an independent flow channel unit, it is possible to set the flow channel member 41 and the prism 14 individually in the immobilizing device 10 or the assay device 11, or build them in these devices.

Although the SPR assay apparatus has been described as an example of the assay apparatuses utilizing attenuated total reflection, a leaky mode sensor can be mentioned as another example of the assay apparatuses utilizing the attenuated total reflection. The leaky mode sensor consists of a dielectric material, a cladding layer overlaid on the dielectric material, and an optical waveguide layer overlaid on the cladding layer, wherein these layers constitute a thin film. A first surface of the thin film is a sensor surface, whereas a second surface of the thin film is a light incident surface. When the light incident on the light incident surface satisfies the condition for the total reflection, part of the light passes through the cladding layer, and enters the optical waveguide layer. Then, a guided mode is excited responsively in the optical waveguide layer, attenuating the reflected light on the light incident surface. The incident angle at which the guided mode is excited varies depending upon the refraction index of the medium positioned on the sensor surface, like as the surface plasmon resonance. Therefore, it possible to measure the chemical reaction on the sensor surface by detecting the attenuation of the reflected light.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A fluid feeding system comprising:
   a flow channel unit comprising at least a flow channel for feeding a sample fluid containing a sample to a sensor surface for detecting reaction of said sample, an inlet opening for introducing said sample fluid into said flow channel, an outlet opening for draining said sample fluid out of said flow channel, and pipette catchers formed at said inlet and outlet openings; and
   a fluid feeding apparatus comprising a pipette head having a couple of pipettes for sucking and ejecting said sample fluid, a device for moving said pipette head to said flow channel unit as positioned removably on a designated stage, and pressing ends of said pipettes onto said pipette catchers, to inject said sample fluid into said flow channel, wherein either said ends of said pipettes or said pipette catchers are formed from a soft material so as to be deformed resiliently when said ends of said pipettes are pressed onto said pipette catchers.

2. A fluid feeding system as claimed in claim 1, wherein said pipette catchers are formed from said soft material, whereas a boss is formed on said end of each of said pipettes such that said boss is pressed onto said pipette catcher.

3. A fluid feeding system as claimed in claim 2, wherein each of said pipette catchers is provided with a recess for fitting said boss when said end of said pipette is pressed onto said pipette catcher.

4. A fluid feeding system as claimed in claim 1, wherein each of said pipette catchers is formed from said soft material, and has a boss that is depressed as said end of said pipette is pressed onto said pipette catcher.

5. A fluid feeding system as claimed in claim 1, wherein said pipette catcher is formed from said soft material integrally with rigid body parts of said flow channel unit, which are formed from a rigid material, by two-color molding.

6. A fluid feeding system as claimed in claim 1, wherein said end of said pipette is formed from said soft material, whereas other portion of said pipette is formed from a rigid material integrally with said end by two-color molding.

7. A fluid feeding system as claimed in claim 1, wherein said fluid feeding apparatus further comprises a device for controlling pressure applied from said ends of said pipettes onto said pipette catchers.

8. A fluid feeding method for feeding a fluid to a flow channel by use of pipettes, comprising steps of:

positioning a flow channel unit on a stage, said flow channel unit comprising said flow channel, an inlet opening for introducing said fluid into said flow channel, an outlet opening for draining said fluid out of said flow channel, and pipette catchers formed at said inlet and outlet openings;

moving a pipette head to said flow channel unit as positioned on said stage, said pipette head having a couple of pipettes for sucking and ejecting said fluid;

pressing ends of said pipettes onto said pipette catchers, wherein either said ends of said pipettes or said pipette catchers are formed from a soft material so as to be deformed resiliently according to a pressure applied thereto; and injecting said fluid into said flow channel through said pipettes while said ends of said pipettes being pressed onto said pipette catchers.

9. A flow channel unit comprising at least a flow channel for feeding a sample fluid containing a sample to a sensor surface for detecting reaction of said sample, an inlet opening for introducing said sample fluid into said flow channel, an outlet opening for draining said sample fluid out of said flow channel, and pipette catchers formed at said inlet and outlet openings, for catching ends of pipettes while said sample fluid is being injected into said flow channel through said pipettes, wherein said pipette catchers are formed from a soft material so as to be deformed resiliently when said ends of said pipettes are pressed onto said pipette catchers.

10. A flow channel unit as claimed in claim 9, wherein said pipette catcher has a circular catching surface around a rim of each of said inlet and outlet openings.

11. A flow channel unit as claimed in claim 10, wherein each of said pipette catchers is provided with a recess recessed from said catching surface, such that a boss formed on said end of said pipette is fitted in said recess.

12. A flow channel unit as claimed in claim 10, wherein each of said pipette catchers has a boss that protrudes from said catching surface, and is resiliently depressed when said end of said pipette is pressed onto said pipette catcher.

13. A flow channel unit as claimed in claim 9, wherein said pipette catcher is formed as an extension of soft body parts that constitute an inner wall of said flow channel, and said soft body parts are formed from said soft material.

14. A flow channel unit as claimed in claim 13, wherein said flow channel unit consists of said soft body parts and rigid body parts that are harder than said soft body parts, and said soft body parts and said rigid body parts are formed integrally by two-color molding, using a soft resin material and a rigid resin material respectively.

15. A flow channel unit as claimed in claim 14, wherein said soft resin material is amorphous polyolefin elastomer, and said rigid resin material is crystalline polyolefin.

* * * * *